(12) United States Patent
Tan

(10) Patent No.: US 8,545,480 B2
(45) Date of Patent: Oct. 1, 2013

(54) ANIMAL FECES SUCTION APPARATUS

(76) Inventor: Ta-Lun Tan, Taipei (TW)

( * ) Notice: Subject to any disclaimer, the term of this patent is extended or adjusted under 35 U.S.C. 154(b) by 0 days.

(21) Appl. No.: 13/194,166

(22) Filed: Jul. 29, 2011

(65) Prior Publication Data

US 2012/0029485 A1 Feb. 2, 2012

(30) Foreign Application Priority Data

Jul. 30, 2010 (TW) .............................. 99214682 U

(51) Int. Cl.
*A61B 19/00* (2006.01)

(52) U.S. Cl.
USPC ........................................... 604/540; 604/19

(58) Field of Classification Search
USPC .................................................. 604/540, 19
See application file for complete search history.

(56) References Cited

U.S. PATENT DOCUMENTS 5,443,445 A * 8/1995 Peters et al. .................... 604/27
6,585,720 B2 * 7/2003 Lapcevic ...................... 604/540

* cited by examiner

*Primary Examiner* — Leslie Deak
*Assistant Examiner* — Sara Sass
(74) *Attorney, Agent, or Firm* — Morris Manning & Martin LLP; Tim Tingkang Xia, Esq.

(57) ABSTRACT

An animal feces suction apparatus includes a tubular body having a stretching portion and a connection portion, a feces suction channel formed in the tubular body, a plurality of liquid channels disposed in a tube wall of the tubular body and formed with a plurality of liquid outlets in the stretching portion, an aspirator connected to the connection portion and communicated with the feces suction channel so as to generate a suction force within the feces suction channel, and a liquid supplying device connected to the connection portion and communicated with the liquid channels so as to provide a liquid to a large intestine of an animal via the liquid outlets. The stretching portion is stretched into the large intestine of the animal and transmits the liquid so as to soften the feces, and the feces is then sucked out from the large intestine through the feces suction channel by the suction force.

9 Claims, 6 Drawing Sheets

ANIMAL FECES SUCTION APPARATUS

BACKGROUND OF THE INVENTION

1. Field of the Invention

The present invention relates to animal feces suction apparatuses, and more particularly, to an animal feces suction apparatus applicable to cure an animal's constipation.

2. Description of Related Art

Nowadays, due to a variety of factors such as a low fertility rate, urbanization, the singleton principle, popularization of a nuclear family mode and the like, more and more people adopt pets for their homes. Other than feeding a general economic animal, a modern pet owner specifically sees a pet as a life companion and as a spiritual security. When the pet is ill, the pet is often sent to a hospital immediately by the owner who cares for the pet intensively and devotes all of his attention to the pet. As a result, the health care market for pets is emerging greatly in light of the intensive attention and caring attitude of the pet owner for the pet's physiological and mental status.

Generally speaking, an intestine peristalsis is getting worse because the pet is getting uneven nutrition and lacks fiber among its foodstuff. Also, genetic defects of the pet itself may cause the peristalsis. Therefore, feces is usually accumulated in the colon. In this case, a usual veterinary treatment is to remove the feces by using an enema first. If the accumulation of feces is serious, a veterinarian will dig the accumulated feces out with his hand by using a finger entering the rectum through the anus of the pet. However, the feces is usually accumulated in a colon portion deeper than the rectum. Thus, the feces is not readily cleaned out thoroughly beyond the length of a human finger.

If the feces accumulation is too serious, another veterinary treatment for the pet is to perform colon surgery in order to cut off an end of the colon so as to solve completely the frequent occurrence of accumulated feces. While the total length of the large intestine thereby becomes shorter, the amount of water absorbed from the feces will be decreased, so as to increase the hardening and accumulation of the feces. Thus, the problem of pet constipation may not be well resolved. However, the colon surgery has various kinds of heath risks for an old or weak pet and will not be appropriate for all pets.

SUMMARY OF THE INVENTION

According to certain embodiments, an approach is provided to resolve the problematic accumulation of animal feces in the large intestine by providing an animal feces suction apparatus. The apparatus is stretched into the large intestine of the animal. After softening the feces with a liquid, the feces are sucked out from the large intestine. Thus, not only is a process better and more efficient than digging out the feces by the veterinarian with his or her hands achieved, but also a safer operation is feasible, considering the risks of infections and the complications from colon surgery.

The animal feces suction apparatus of the present invention comprises a tubular body, a feces suction channel, a plurality of liquid channels, an aspirator, and a liquid supplying device. The tubular body includes a connection portion and a stretching portion for stretching into the large intestine of the animal. The feces suction channel is formed in the tubular body. The liquid channels are disposed in a tube wall of the tubular body and formed with a plurality of liquid outlets on the stretching portion.

The aspirator is connected to the connection portion and communicated with the feces suction channel so as to generate a suction force within the feces suction channel. The liquid supplying device is connected to the connection portion and communicated with the liquid channels so as to provide the liquid to the large intestine of the animal via the liquid outlets, wherein the liquid is water or a lubricant. The stretching portion is stretched into the large intestine of the animal and transmits the liquid via the liquid outlets so as to soften the feces, and the feces is sucked out from the large intestine of the animal through the feces suction channel by the suction force generated by the aspirator.

In one embodiment, the aspirator further includes a removable storing container which has a feces storage space therein so as to store the feces sucked out from the large intestine.

While compared with the prior art in which the veterinarian merely solves the problem of pet constipation by using his finger or by colon surgery, the animal feces suction apparatus of the present invention can be stretched into the large intestine of the animal by the tubular body and can provide the liquid to the large intestine of the animal via the liquid channels and the liquid outlets by the liquid supplying device so as to soften the dry and hard feces. The apparatus generates the suction force within the feces suction channel of the tubular body by the aspirator after the feces is softened such that the feces is sucked out from the large intestine of the animal and stored in the feces storage space in the removable storing container of the aspirator.

According to the foregoing utilization method of the animal feces suction apparatus of the present invention, proper feces removal can be achieved rather than digging out the feces by the hand of the veterinarian. Also, the risks for the pet facing colon surgery will be avoided. Hence, the present invention is innovative and has excellent clinical results.

DETAILED DESCRIPTION OF PREFERRED EMBODIMENTS

Embodiments of the present invention are discussed in the following description for one skilled in the art to implement according to the invention.

Figure 1:
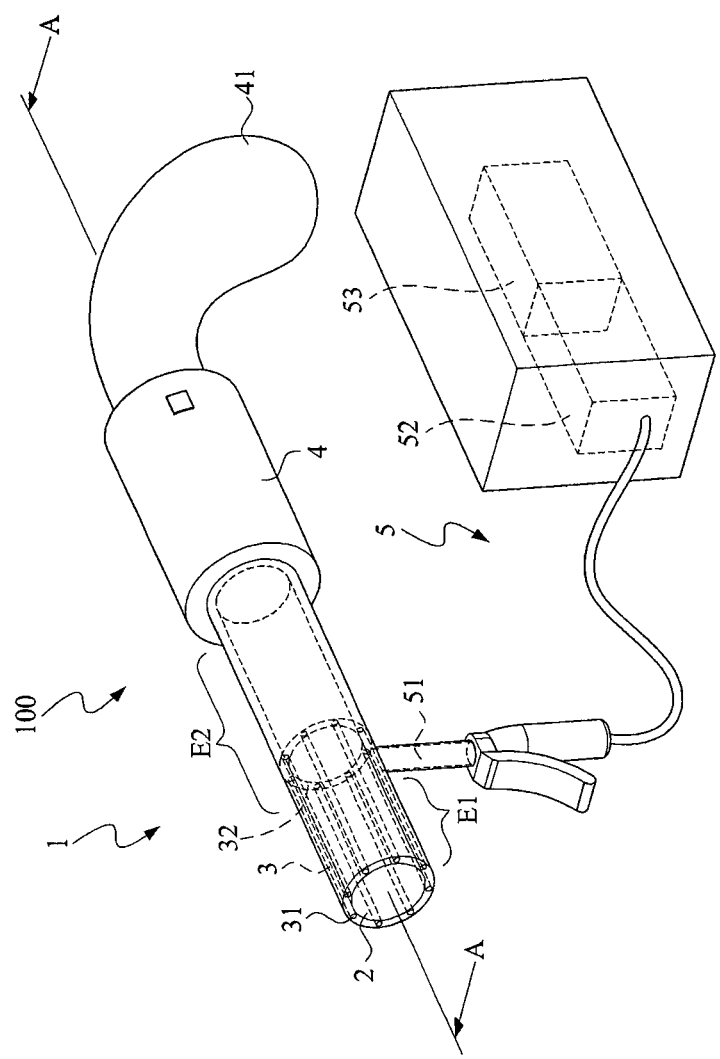
FIG. 1 is a schematic perspective diagram of an animal feces suction apparatus in accordance with a first embodiment.
Figure 2:
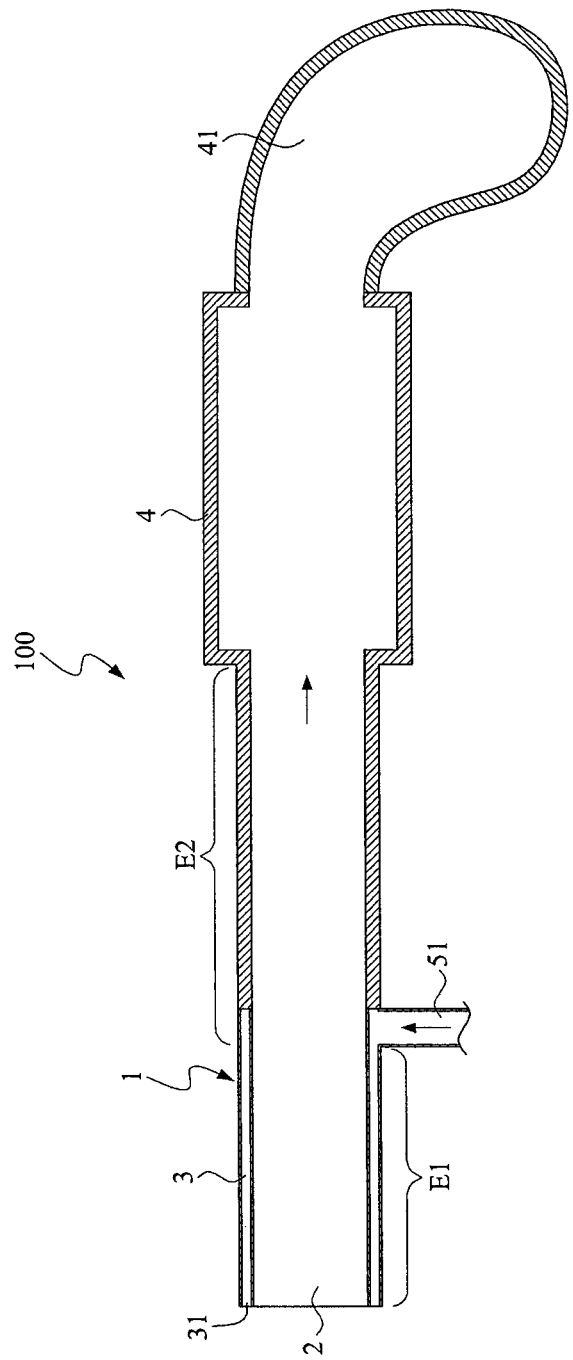
FIG. 2 is a schematic sectional diagram of the animal feces suction apparatus along the cross-section line A-A in FIG. 1 in accordance with the first embodiment.

FIG. 1 and FIG. 2 are a schematic perspective diagram and a schematic sectional diagram along the cross-section line A-A in FIG. 1, respectively, of an animal feces suction apparatus 100 made in accordance with a first embodiment. As illustrated, the animal feces suction apparatus 100 comprises a tubular body 1, a feces suction channel 2, a plurality of liquid channels 3, an aspirator 4, and a liquid supplying device 5.

The tubular body 1 can be manufactured by a plastic injection molding method or can be made of metal, rubber or silicone. The front and back section of the tubular body 1 are distinguished as a stretching portion E1 and a connection portion E2, respectively. The stretching portion E1 is used to be stretched into a large intestine of an animal, and the connection portion E2 is used to connect the aspirator 4 and the liquid supplying device 5. The feces suction channel 2 is formed at a hollow location in the tubular body 1. The liquid channels 3 are disposed circularly in the tube wall of the tubular body 1 and are formed with a plurality of liquid outlets 31 in the stretching portion E1. At the same time, the liquid channels 3 are communicated with each other via an annular channel 32 in the tube wall of the tubular body 1.

The aspirator 4 includes a pump (not shown) and a removable storing container 41. The removable storing container 41 can be a bag or a box-like object and has a feces storage space therein. In this first embodiment, the removable storing container 41 is a bag embedded in the back end of a housing of the aspirator 4 which can be assembled and disassembled easily. The aspirator 4 is connected to the connection portion E2 and is communicated with the feces suction channel 2 so as to allow the pump (not shown) to generate a suction force within the feces suction channel 2. In this first embodiment, the aspirator 4 is directly mounted on the connection portion E2.

The liquid supplying device 5 includes a transfusion pipe 51, a pressure pump 52 and a liquid storage tank 53. The transfusion pipe 51 communicates with the liquid storage tank 53, the liquid storage tank 53 stores a liquid, and the pressure pump 52 presses the liquid, wherein the liquid used to soften the feces 300 can be either water, or a lubricant such as glycerin, and so on, and the liquid can be further added with any applicable compound that may accelerate the softening of the feces.

The liquid supplying device 5 is communicated with the annular channel 32 in the tube wall of the tubular body 1 at the connection portion E2 via the transfusion pipe 51 so as to be communicated with the liquid channels 3. The liquid is pressed and transmitted into the large intestine of the animal through the liquid channels 3 when the pressure pump 52 is operated.

Figure 3:
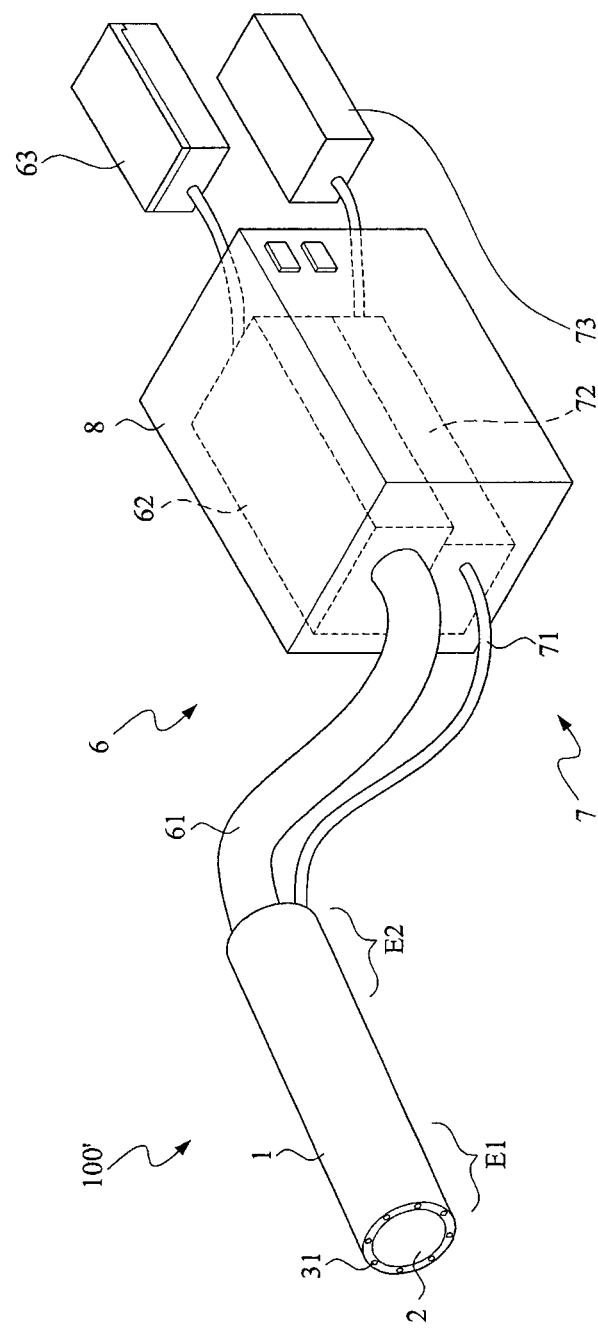
FIG. 3 is a schematic structural diagram of the animal feces suction apparatus in accordance with a second embodiment.

FIG. 3 is a schematic structural diagram of the animal feces suction apparatus 100' made in accordance with the second embodiment. As illustrated, this second embodiment is similar to the first embodiment, in which the animal feces suction apparatus 100' comprises the tubular body 1, the feces suction channel 2 formed at the hollow location in the tubular body 1, and the liquid channels 3 (not shown) disposed circularly in the tube wall of the tubular body 1. The liquid channels 3 are formed with the plurality of liquid outlets 31 on the stretching portion E1 of the tubular body 1 and are communicated with each other in the tube wall of the tubular body 1.

In this second embodiment, the animal feces suction apparatus 100' further comprises an operation unit 8, an aspirator 6, and a liquid supplying device 7. The aspirator 6 includes a communication pipe 61, a pump 62, and a removable storing container 63. The liquid supplying device 7 includes a transfusion pipe 71, a pressure pump 72, and a liquid storage tank 73. The operation unit 8 integrates the pump 62 and the pressure pump 72 by electrical configurations such that a user can perform a start-up control or a shut-down control, respectively, of the pump 62 and the pressure pump 72 by operating buttons provided on the operation unit 8, so as to facilitate more conveniently the operation of the aspirator 6 and the liquid supplying device 7.

The communication pipe 61 is connected at one end to the connection portion E2 which is communicated with the feces suction channel 2 while the communication pipe 61 is also communicated at its opposite end through the pump 62 with the removable storing container 63. The transfusion pipe 71 is communicated at one end with the liquid channels 3 and at its opposite end through the pressure pump 72 with the liquid storage tank 73. In this second embodiment, while having a different configuration for the tubular body 1, the removable storing container 63 can be constituted as a box-shaped object having a large volume, so as to have a larger feces storage space for storing more feces at one time.

Figure 4:
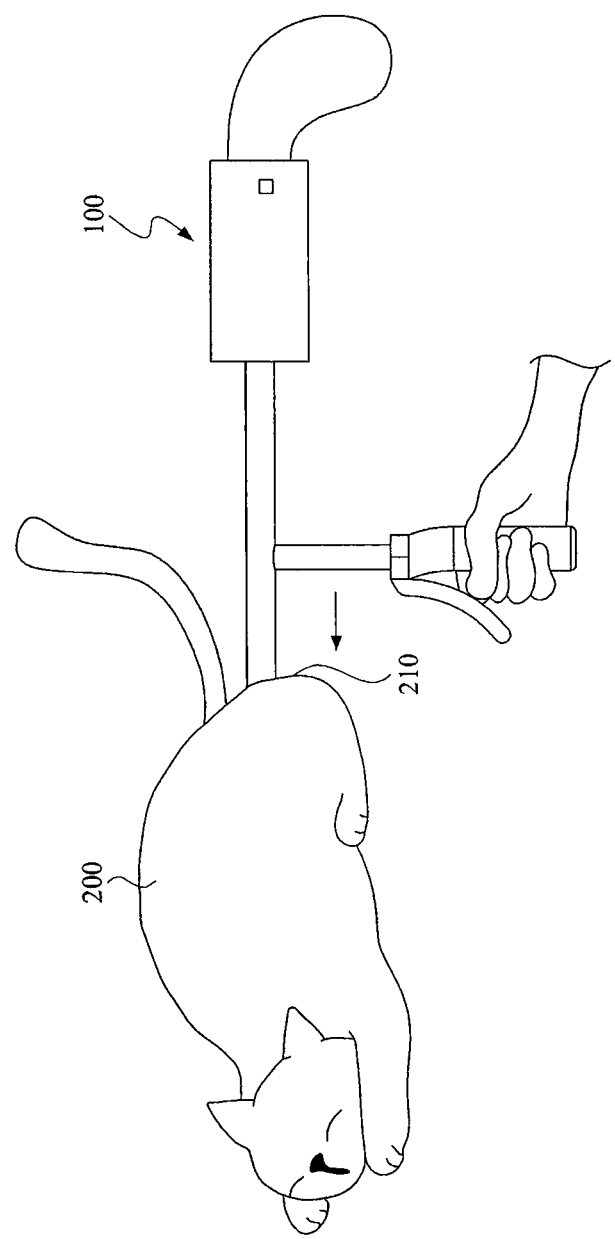
FIG. 4 is a schematic diagram showing application of the animal feces suction apparatus in accordance with the first embodiment.

FIG. 4 is a schematic diagram showing application of the animal feces suction apparatus 100 in accordance with the first embodiment. As illustrated, the animal 200, such as a cat and the like, can be first anesthetized totally or locally, and then the stretching portion E1 of the animal feces suction apparatus 100, being disinfected, is inserted into the colon in the large intestine of the animal 200 through an anus 210 of the animal 200. Next, returning to FIG. 1, the pressure pump 52 of the liquid supplying device 5 is actuated, and the liquid is pressed so as to be injected into the liquid channels 3 through the transfusion pipe 51.

Figure 5:
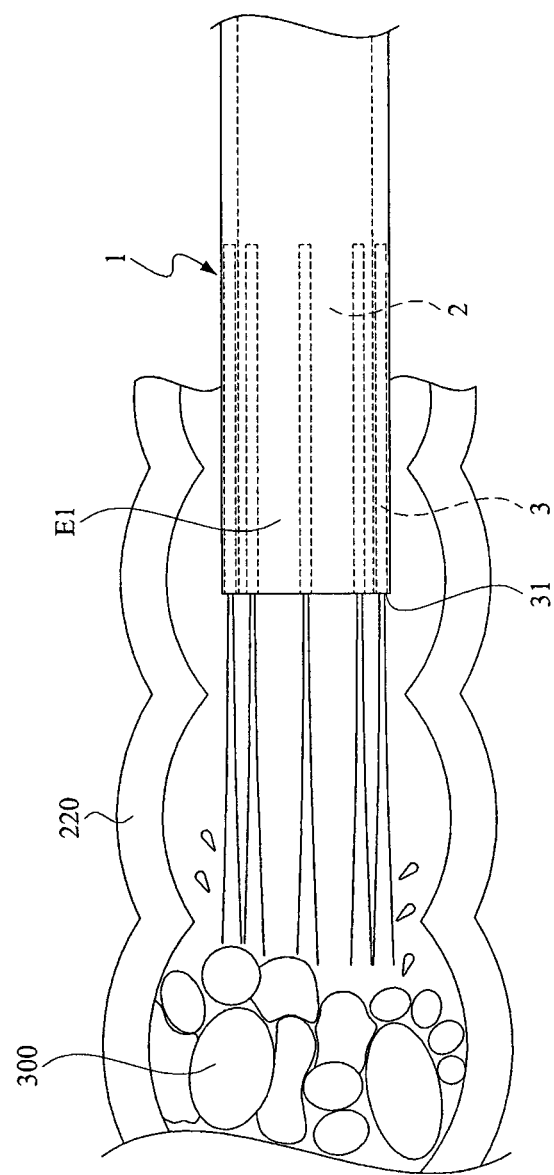
FIG. 5 and FIG. 5A are schematic diagrams showing utilization of the animal feces suction apparatus in accordance with the first embodiment.
Figure 5A:
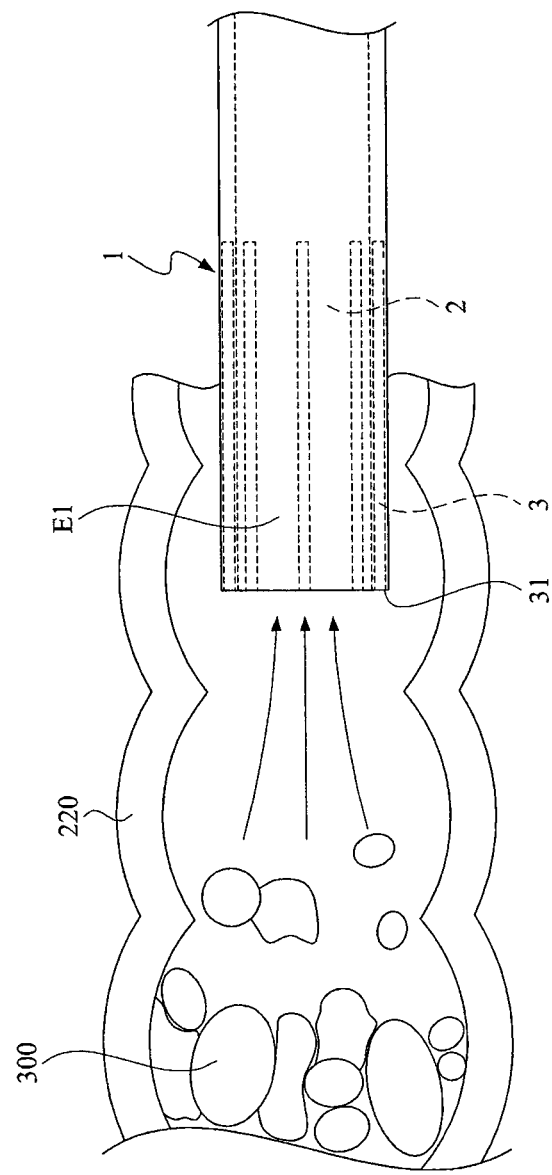

FIG. 5 and FIG. 5A are schematic diagrams showing utilization of the animal feces suction apparatus in accordance with the first embodiment. As illustrated in FIG. 5, the liquid passes through the liquid channels 3 and is sprayed from the liquid outlet 31 on the stretching portion E1 into the large intestine 220. The liquid is sprayed on a feces block stacked with dry and hard feces. The feces block can be decomposed as small feces 300 while an intestinal wall can be lubricated after the liquid is infiltrated into the feces block.

As illustrated in FIG. 5A, the pump of the aspirator is actuated to generate a suction force within the feces suction channel 2 such that the small feces 300 is sucked out from the large intestine 220 of the animal through the feces suction channel 2 and stored in the feces storage space of the removable storing container after the feces block is decomposed as soft and small feces 300 and the intestinal wall is lubricated sufficiently.

It can be known from the foregoing embodiments of the present invention that the present invention is indeed very useful. However, the foregoing illustrations merely concern the preferred embodiments of the present invention. One skilled in the art can perform a variety of modifications and variations based on the foregoing embodiments of the present invention. However, these various kinds of modifications and variations based on the foregoing embodiments of the present invention are still within the following scope of the following claims.

What is claimed is:

1. An animal feces suction apparatus comprising:
 a tubular body including a connection portion and a stretching portion for stretching into a large intestine of an animal;
 a feces suction channel formed in the tubular body;
 a plurality of liquid channels disposed in a tube wall of the tubular body in parallel to the feces suction channel, and formed with a plurality of liquid outlets in the stretching portion;
 an aspirator connected to the connection portion and communicated with the feces suction channel so as to generate a suction force within the feces suction channel; and
 a liquid supplying device connected to the connection portion and communicated with the liquid channels so as to provide liquid to the large intestine of the animal via the liquid outlets, wherein the liquid softens the feces, and the feces is sucked out from the large intestine of the animal through the feces suction channel by the suction force generated by the aspirator;

wherein the aspirator and the liquid supplying device are capable of operating respectively or simultaneously, and wherein each of the liquid channels is isolated from the feces suction channel by the tube wall such that when the aspirator and the liquid supplying device operate simultaneously, the suction force generated by the aspirator within the feces suction channel does not interfere with the liquid being provided in the liquid channels to the large intestine via the liquid outlets.

2. The animal feces suction apparatus of claim 1, wherein the aspirator includes a feces storage space for storing the feces sucked out from the large intestine.

3. The animal feces suction apparatus of claim 2, wherein the aspirator includes a removable storing container, and the feces storage space is positioned in the removable storing container.

4. The animal feces suction apparatus of claim 1, wherein the liquid is water or lubricant.

5. The animal feces suction apparatus of claim 1, wherein the aspirator includes a pump for generating the suction force.

6. The animal feces suction apparatus of claim 1, wherein the liquid supplying device includes a pressure pump for pumping the liquid.

7. The animal feces suction apparatus of claim 1, wherein the liquid channels are disposed in the tube wall of the stretching portion of the tubular body.

8. The animal feces suction apparatus of claim 1, wherein an inner diameter of the feces suction channel is larger than an inner diameter of each of the liquid channel.

9. The animal feces suction apparatus of claim 1, wherein the stretching portion is stretchable from the connection portion such that a length of the stretching portion is variable.

\* \* \* \* \*